(12) United States Patent
Bolze et al.

(10) Patent No.: US 11,813,362 B2
(45) Date of Patent: Nov. 14, 2023

(54) FILM-COATED TABLET COMPRISING A TRIAZINE DERIVATIVE FOR USE IN THE TREATMENT OF DIABETES

(71) Applicant: Poxel, Lyons (FR)

(72) Inventors: Sébastien Bolze, Massieux (FR); Maxime Laugier, Royat (FR)

(*) Notice: Subject to any disclaimer, the term of this patent is extended or adjusted under 35 U.S.C. 154(b) by 46 days.

(21) Appl. No.: 17/251,355

(22) PCT Filed: Jun. 11, 2019

(86) PCT No.: PCT/EP2019/065158
§ 371 (c)(1),
(2) Date: Dec. 11, 2020

(87) PCT Pub. No.: WO2019/238647
PCT Pub. Date: Dec. 19, 2019

(65) Prior Publication Data
US 2021/0212951 A1 Jul. 15, 2021

(30) Foreign Application Priority Data

Jun. 14, 2018 (EP) .................................... 18305730

(51) Int. Cl.
*A61K 9/28* (2006.01)
*A61K 9/20* (2006.01)
*A61K 31/53* (2006.01)

(52) U.S. Cl.
CPC .......... *A61K 9/2866* (2013.01); *A61K 9/2009* (2013.01); *A61K 9/2013* (2013.01); *A61K 9/2054* (2013.01); *A61K 9/2095* (2013.01); *A61K 9/2893* (2013.01); *A61K 31/53* (2013.01)

(58) Field of Classification Search
CPC .......... A61K 9/14; A61K 9/16; A61K 9/1605; A61K 9/20; A61K 9/2004; A61K 9/2009; A61K 9/2013; A61K 9/2018; A61K 9/2022; A61K 9/205; A61K 9/2054; A61K 9/2059; A61K 9/2072; A61K 9/2077; A61K 9/2095; A61K 9/28; A61K 9/2806; A61K 9/2813; A61K 9/2893
See application file for complete search history.

(56) References Cited

U.S. PATENT DOCUMENTS

| | | | |
|---|---|---|---|
| 3,287,366 A | 11/1966 | Newman et al. | |
| 7,034,021 B2 | 4/2006 | Moinet et al. | |
| 7,452,883 B2 | 11/2008 | Moinet et al. | |
| 7,501,511 B2 | 3/2009 | Moinet et al. | |
| 7,767,676 B2 | 8/2010 | Moinet et al. | |
| 8,217,040 B2 | 7/2012 | Moinet et al. | |
| 8,227,465 B2 | 7/2012 | Moinet et al. | |
| 8,461,331 B2 | 6/2013 | Helmreich et al. | |
| 8,592,370 B2 | 11/2013 | Mesangeau et al. | |
| 8,742,102 B2 | 6/2014 | Helmreich et al. | |
| 8,742,103 B2 | 6/2014 | Cravo et al. | |
| 8,791,115 B2 | 7/2014 | Moinet et al. | |
| 8,846,911 B2 | 9/2014 | Maillard et al. | |
| 8,937,066 B2 | 1/2015 | Mesangeau et al. | |
| 8,980,828 B2 | 3/2015 | Mesangeau et al. | |
| 9,035,048 B2 | 5/2015 | Cravo et al. | |
| 9,271,984 B2 | 3/2016 | Fouqueray et al. | |
| 2006/0223803 A1 | 10/2006 | Moinet et al. | |
| 2010/0256368 A1 | 10/2010 | List et al. | |
| 2013/0177604 A1 | 7/2013 | Baron et al. | |
| 2015/0246045 A1 | 9/2015 | Klein et al. | |
| 2017/0119853 A1 | 5/2017 | Shannon | |
| 2017/0266152 A1 | 9/2017 | Broedl et al. | |
| 2017/0304262 A1 | 10/2017 | Naik et al. | |

FOREIGN PATENT DOCUMENTS

| | | | | |
|---|---|---|---|---|
| CN | 102387783 A | | 3/2012 | |
| EP | 2468261 A1 | * | 6/2012 | ........... A61K 31/165 |
| EP | 2355829 B1 | | 12/2014 | |
| JP | 2009137996 A | | 6/2009 | |
| JP | 4864088 B2 | | 1/2012 | |
| JP | 5414986 B2 | | 2/2014 | |
| JP | 6141915 B2 | | 6/2017 | |
| TW | 200504037 A | | 2/2005 | |
| WO | WO-99/31088 A1 | | 6/1999 | |
| WO | 2001055122 A1 | | 8/2001 | |
| WO | WO-01/55122 A1 | | 8/2001 | |
| WO | WO-2004/089917 A2 | | 10/2004 | |
| WO | WO-2005/070905 A1 | | 8/2005 | |
| WO | 2007079916 A2 | | 7/2007 | |

(Continued)

OTHER PUBLICATIONS

Poxel Corporate Presentation, "Imeglimin" and "PXL770," presented by Poxel in Jan. 2017, 39 pages.
Arnouts, et al., "Glucose-lowering drugs in patients with chronic kidney disease: a narrative review on pharmacokinetic properties," Nephrol Dial Transplant vol. 29, pp. 1284-1300, Oxford University Press, England, 2013.
Banquet, S., et al., "Arteriogenic therapy by intramyocardial sustained delivery of a novel growth factor combination prevents chronic heart failure," *Circulation* 124(9):1059-1069, Lippincott Williams and Wilkins Ltd., United States (2011).
Baumann, et al., "Anti-inflammatory therapy in type 1 diabetes," Abstract, Curr. Diab. Rep., vol. 12, Issue 5, pp. 499-509, 2012.

(Continued)

*Primary Examiner* — Micah Paul Young
(74) *Attorney, Agent, or Firm* — Goodwin Procter LLP (57) ABSTRACT

This invention pertains to a film-coated tablet comprising an inner core and an external coating, wherein the inner core comprises a high proportion of a specific triazine derivative, namely 2-amino-3,6-dihydro-4-dimethylamino-6-methyl-1,3,5-triazine and pharmaceutically acceptable salts thereof, and a specific binder. It is also directed to the use of these tablets in the treatment of diabetes and/or complications thereof. This invention is further directed to a specific process for the manufacture of these film-coated tablets, which involves a granulation step in a high-shear mixer.

23 Claims, 1 Drawing Sheet

(56) References Cited

FOREIGN PATENT DOCUMENTS

| WO | WO-2007/079915 A2 | 7/2007 | |
| WO | WO-2007079914 A2 * | 7/2007 | ............ A61K 31/53 |
| WO | WO-2009/062483 A2 | 5/2009 | |
| WO | 2009095159 A1 | 8/2009 | |
| WO | 2009141040 A2 | 11/2009 | |
| WO | 2010012746 A2 | 2/2010 | |
| WO | 2010066326 A1 | 6/2010 | |
| WO | WO-2010066901 A2 | 6/2010 | |
| WO | WO-2011006984 A1 | 1/2011 | |
| WO | 2011154497 A1 | 12/2011 | |
| WO | WO-2011/154497 A1 | 12/2011 | |
| WO | WO-2011154497 A1 * | 12/2011 | ............ A61K 31/53 |
| WO | 2012072663 A1 | 6/2012 | |
| WO | WO-2014/161919 A1 | 10/2014 | |
| WO | WO-2014161919 A1 | 10/2014 | |
| WO | WO-2019/069230 A1 | 4/2019 | |
| WO | WO-2019069230 A1 | 4/2019 | |
| WO | WO-2019/236844 A1 | 12/2019 | |
| WO | WO-2019236844 A1 | 12/2019 | |

OTHER PUBLICATIONS

Bezold M.A., "Vergleich der Auswirkung einer oralen therapie mit metformin und EMD 387008 auf renale Schaden im Tiermodell der diabetogenen ZDF-Ratte/ comparing the effects of oral therapy with metformin and EMD387008 to renal damage in the animal model of the diabetic ZDF rat," Doctoral Thesis p. 108 (2010).

Bristol-Myers Squibb., Glucophage package insert. U.S. Food and Drug Administration website <https://www.accessdata.fda.gov/drugsatfda_docs/label/2017/020357s037s039,021202s021s023lbl.pdf>. Revised Apr. 2017. Accessed May 10, 2021.

Ceia, F., et al., "Prevalence of chronic heart failure in Southwestern Europe: the EPICA study," *Eur J Heart Failure* 4(4):531-539, Wiley-Blackwell, United States (2002).

Cravo, Declaration Under Rule 132 by Dr. Daniel Cravo, Mar. 5, 2014, from U.S. Appl. No. 13/703,138.

Devereux, R.B., et al., "Congestive heart failure despite nonnal left ventricular systolic function in a population-based sample: the Strong Heart Study," *Am J Cardiol* 86(10):1090-1096, Elsevier Inc., United States (2000).

Donath, M. et al., "Mechanisms of ß-Cell Death in Type 2 Diabetes," Diabetes, vol. 54, Supplement 2, pp. S108-S113, 2005.

Dubourg, J., et al., "843—Imeglimin monotherapy in Japanese patients with type 2 diabetes: results from a randomised, 24-week, double-blind, placebo controlled, phase lib trial," 53r d EASD Annual Meeting of the European Association for the Study of Diabetes (Sep. 11-15, 2017 , Session F-PS066 Novel A roaches to Glucose-Lowerin : Abstract 843, 1 a e 2017.

Dubourg, J., et al., "Imeglimin monotherapy in Japanese patients with type 2 diabetes: results from a randomized, 24-week, double-blind, placebo-controlled, phase lib trial," 53$^{rd}$ *EASD Annual Meeting of the European Association for the Study of Diabetes* (Sep. 11-15, 2017), Session PS066 Novel Approaches to glucose-lowering: Poster 843, 1 page (2017).

Dubourg; J. et al., "843—Imeglimin monotherapy in Japanese patients with type 2 diabetes: results from a randomised, 24-week, double-blind, placebo controlled, phase lib trial, Session F PS066 novel Approaches to glucose-lowering," (2017), Abstract.

Dubourg; J. et al., "Imeglimin monotherapy in Japanese patients with type 2 diabetes: results from a randomised, 24-week, double-blind, placebo-controlled, phase lib trial," EASD 2017 Session PS066 Novel Approaches to glucose-lowering, Poster, Poxel (2017).

Eurasia Patent Office, Partial English translation of http:/mccli.ru/doc/a793705 cited Application No. EA201201623 (Fouqueray et al), Mar. 25, 2015, from U.S. Appl. No. 13/703,138.

Fang, Y., et al., "Improvement of left ventricular diastolic function induced by -blockade: a comparison between nebivolol and metoprolol," *Journal of Molecular and Cellular Cardiology* 51(2):168-176, Academic Press Inc., United States (2011).

Fang, Y.H., et al., "Heart rate reduction induced by the if current inhibitor ivabradine improves diastolic function and attenuates cardiac tissue hypoxia," *Journal of Cardiovascular Pharmacology* 59(3):260-267, Lippincott Wiliams and Wilkins Ltd., United States (2012).

Fonarow, G.C., et al., "Characteristics, treatments, and outcomes of patients with preserved systolic function hospitalized for heart failure: a report from the OPTIMIZE-HF Registry," *J Am College Cardio/* 50(8):768-777, Elsevier, Netherlands (2007).

Fonseca, "Defining and Characterizing the Progression of Type 2 Diabetes," Diabetes Care, vol. 32, Issue 2, pp. SI51-SI56, 2009.

Fraccarollo, D., et al., "Improvement in left ventricular remodeling by the endothelial nitric oxide synthase enhancer A VE9488 after experimental myocardial infarction," *Circulation* 118:818-827, Lippincott Williams and Wilkins Ltd., United States (2008).

From, A.M., et al., "Heart Failure with Preserved Ejection Fraction: Pathophysiology and Emerging Therapies," *Cardiovascular Therapeutics* 29(4):E6-E21, Wiley-Blackwell Publishing Ltd., United Kingdom (2011).

Gillebert, T.C., et al., "Intracavitary ultrasound impairs left ventricular performance: presumed role of endocardial endothelium," *Am J Physiol* 263(6):H857-H865, American Physiological Society, United States (1992).

Gomez, E., et al., "Reduction of heart failure by phannacological inhibition or gene deletion of protein tyrosine phosphatase IB," *Journal of Molecular and Cellular Cardiology* 52(6):1257-1264, Academic Press Inc., United States (2012).

Hallakou-Bozec, Declaration Under Rule 132 by Dr. S. Hallakou-Bozec, May 21, 2015, from U.S. Appl. No. 13/703,147.

Hallakou-Bozec, et al., "Mechanism of action of Imeglimin: A novel therapeutic agent for type 2 diabetes," Diabetes Obes. Metab. vol. 23, pp. 664-673, 2021.

International Search Report and Written Opinion for International Application No. PCT/IB2018/057648, European Patent Office, Netherlands, dated Jan. 22, 2019, 11 pages.

Kitzman, D.W., et al., "Importance of heart failure with preserved systolic function in patients >or= 65 years of age. CHS Research Group. Cardiovascular Health Study," *Am J Cardiol* 87(4):413-419, Elsevier Inc., United States (2001).

Knowler, et al., "Reduction in the Incidence of Type 2 Diabetes with Lifestyle Intervention or Metformin," The New England Journal of Medicine, vol. 346, Issue 6, pp. 393-403, 2002.

Komajda, M., and Lam, C.S.P., "Heart failure with preserved ejection fraction: a clinical dilemma," *Eur Heart J* 35(16):1022-1032, Oxford University Press, United Kingdom (2014).

Krischer, J., et al., "Screening Strategies for the Identification of Multiple Antibody-Positive Relatives of Individuals with Type 1 Diabetes," The Journal of Clinical Endocrinology & Metabolism, vol. 881, Issue 1, pp. 103-108, 2003.

Lachaux, M., "P577 Short- and long-term imeglimin treatment reduces metabolic syndrome related diabetic cardiomyopathy," *European Heart Journal* 38(Suppl_I):ehx501.P577, Oxford University Press, United Kingdom (Aug. 2017).

Lam, C.S.P., et al., "Epidemiology and clinical course of heart failure with preserved ejection fraction," Eur. J Heart Failure 13(1):18-28, Wiley-Blackwell, United States (2011).

Larger, Declaration Under Rule 132 by Dr. E. Larger, May 22, 2015, from U.S. Appl. No. 13/703,147.

Lloyd-Jones, D.M., et al., "Defining and setting national goals for cardiovascular health promotion and disease reduction: the American Heart Association's strategic Impact Goal through 2020 and beyond," *Circulation* 121(4):586-613, Lippincott Williams and Wilkins Ltd., United States (2010).

Marchetti, P., et al., "Pancreatic Islets from Type 2 Diabetic Patients Have Functional Defects and Increased Apoptosis That Are Ameliorated by Metformin," The Journal of Clinical Endocrinology & Metabolism, vol. 89, Issue 11, pp. 5535-5541.

Marin-Penalaver; J.J. et al., "Update on the treatment of type 2 diabetes mellitus," World J. Diabetes 7(17):354-95, Baishideng Publishing Group, United States (2016).

(56) References Cited

OTHER PUBLICATIONS

Matter, C.M., et al., "Effect of NO Donors on LV Diastolic Function in Patients With Severe Pressure-Overload Hypertrophy," *Circulation* 99(18):2396-2401, Lippincott Williams and Wilkins Ltd., United States (1999).

Merabet, N., et al., "Soluble epoxide hydrolase inhibition improves myocardial perfusion and function in experimental heart failure," *Journal of Molecular and Cellular Cardiology* 52(3):660-666, Academic Press Inc., United States (2012).

Modest, E.J., "Chemical and Biological Studies on 1,2-Dihydro-s-triazines. II. Three-Component Synthesis," The Journal of Organic Chemistry, vol. 21, Issue 1, pp. 1-13, 1956.

Modest, E.J., "Chemical and Biological Studies on 1,2-Dihydro-s-triazines. III. Two Component Synthesis," The Journal of Organic Chemistry, vol. 21, Issue 1, pp. 14-20, 1956.

Mulder, P., et al., "Aldosterone synthase inhibition improves cardiovascular function and structure in rats with heart failure: a comparison with spironolactone," *Eur Heart J* 29(17):2171- 2179, Oxford University Press, United Kingdom (2008).

Mulder, P., et al., "Increased Survival After Long-Term Treatment With Mibefradil, a Selective T-Channel Calcium Antagonist, in Heart Failure," *Journal of the American College of Cardiology* 29(2):416-421, Elsevier, Netherlands (1997).

Oghlakian, G.O., et al., "Treatment of Heart Failure With Preserved Ejection Fraction: Have We Been Pursuing the Wrong Paradigm?" *Mayo Clinic Proceedings* 86(6):531-539, Elsevier Science, Netherlands (2011).

Owan, T.E., et al., "Epidemiology of diastolic heart failure," *Frog Cardiofasc Dis* 47(5):320-332, W.B. Saunders Ltd., United Kingdom (2005).

Palsson, R., et al., "Cardiovascular complications of Cardiovascular complications of diabetic kidney disease," *Adv. Chronic. Kidney Dis.* 21(3):273-80, Elsevier, Netherlands (2014).

Palsson; R. et al. "Cardiovascular complications of diabetic kidney disease," Adv. Chronic. Kidney Dis. 21(3):273-80, Elsevier, Netherlands (2014).

PCT International Search Report and Written Opinion, App. No. PCT/EP2011/059589, dated Sep. 20, 2011.

PCT International Search Report and Written Opinion, App. No. PCT/EP2011/059590, dated Sep. 21, 2011.

PCT, International Search Report and Written Opinion, App. No. PCT/US2019/035789, European Patent Office, Netherlands, dated Oct. 10, 2019.

Pirags et al., "Imeglimin, a novel glimin oral anti-diabetic, exhibits good glycemic control in Type 2 diabetic patients," Poster Presentation, Poxel (2010).

Pirags et al., "Imeglimin, a novel glimin oral antidiabetic, exhibits a good efficacy and safety profile in type 2 diabetic patients," Diabetes, Obesity and Metabolism 14(9):852-8 (2012).

Pirags, V. et al., "Imeglimin, a novel glimin oral anti-diabetic, exhibits good glycemic control in Type 2 diabetic patients," Poster Presentation, 1 page, Poxel, France (2010).

Pirags, V., et al., "Imeglimin, a novel glimin oral antidiabetic, exhibits a good efficacy and safety profile in type 2 diabetic patients," *Diabetes, Obesity and Metabolism* 14(9):852-8, Wiley Blackwell Publishing Ltd., United Kingdom (2012).

Poxel, Poxel Corporate Presentation, Imeglimin and PXL770, Jan. 2017.

Poxel, Press Release on Jun. 6, 2017, "Poxel Announces Additional Positive Results for Imeglimin Phase 2b Study in Japan for the Treatment of Type 2 Diabetes," accessed at https://www.poxelpharma.com/en <http://www.poxelpharma.com/en_us/investors/news-events/press-releases/detail/62/poxel>_us/investors/news-events/press-releases/detail/62/poxel <http://www.poxelpharma.com/en_us/investors/news-events/press-releases/detail/62/poxel>announces-additional-positive-results-for-imegliminon Sep. 18, 2020, 4 pages.

Poxel, Press Release, "Poxel Announces Additional Positive Results for Imeglimin Phase 2b Study in Japan for the Treatment of Type 2 Diabetes," Poxel, Jun. 6, 2017.

Redfield, M.M., et al., "Burden of systolic and diastolic ventricular dysfunction in the community: appreciating the scope of the heart failure epidemic," *JAM4* 289(2): 194-202, American Medical Association, United States (2003).

Rembarz, V.G., et al., "Reaktinon mit Natriumdicyanimid," Journal fur praktische Chemie, 4(26):314-318 (1964) (English abstract attached).

Roth, B., et al., "Anthelmintic Agents. 1,2-Dihydro-s-Triazines," Journal of Medicinal Chemistry, American Chemical Society, vol. 6, Issue 4, pp. 370-378, 1963.

Sakamoto, M., et al., "Possibility of a New Therapeutic Strategy for Left Ventricular Dysfunction in Type 2 Diabetes," *Journal of Clinical Medicine Research* 10(11):799-805, Elmer Press Inc., Canada (Nov. 2018).

Silberman, G.A., et al., "Uncoupled cardiac nitric oxide synthase mediates diastolic dysfunction," *Circulation* 121(4):519-528, Lippincott Williams and Wilkins Ltd., United States (2010).

Simmons, K., et al., "Type 1 diabetes: A predictable disease," World J. Diabetes, vol. 6 Issue 3, pp. 380-390, 2015.

Sosenko, J., et al., "A Risk Score for Type 1 Diabetes Derived From Autoantibody-Positive Participants in the Diabetes Prevention Trial-Type I," Diabetes Care, vol. 31, Issue 3, pp. 528-533, 2008.

Stevens, M., et al., "Introduction of a triflate group into sterically hindered positions in I-Aryl-4,6-diamino-1,3,5-triazines and their Dimroth Rearrangement Products," Journal of Heterocyclic Chemistry, vol. 30, Issue 4, pp. 849-853, 1993.

Taiwan Patent Office, English language Summary of Office Action, dated Jun. 19, 2013, Patent Application No. 100120015, including English language summary of TW200504037 A and WO2007/079915A2, from U.S. Appl. No. 13/703,138.

Thornalley, P.J., "Use of aminoguanidine (Pimagedine) to prevent the formation of advanced glycation endproducts," Archives of Biochemistry and Biophysics, vol. 419, Issue 1, pp. 31-40, 2003.

Tiikkainen, M., et al., "Effects of Rosiglitazone and Metformin on Liver Fat Content, Hepatic Insulin Resistance, Insulin Clearance, and Gene Expression in Adipose Tissue in Patients with Type 2 Diabetes," Diabetes, vol. 54, pp. 2169-2176, 2004.

Tuttle et al., "Diabetic Kidney Disease: A Report From an ADA Consensus Conference," Diabetes Care 37(10): 2864-2883, American Diabetes Association (2014).

Tuttle, K.R., et al., "Diabetic Kidney Disease: A Report From an ADA Consensus Conference," *Diabetes Care* 37(10): 2864-2883, American Diabetes Association, United States (2014).

Van Heerebeek, L., et al., "Diastolic stiffness of the failing diabetic heart: importance of fibrosis, advanced glycation end products, and myocyte resting tension," *Circulation* 117(1):43-51, Lippincott Williams and Wilkins Ltd., United States (2008).

Van Heerebeek, L., et al., "The failing diabetic heart: focus on diastolic left ventricular dysfunction," *Curr Diab Rep* 9(1):79-86, Current Medicine Group, United States (2009).

Vercauteren, M., et al., "Improvement of Peripheral Endothelial Dysfunction by Protein Tyrosine Phosphatase Inhibitors in Heart Failure," *Circulation* 114:2498-2507, Lippincott Williams and Wilkins Ltd., United States (2006).

Vuylsteke V. et al., "Imeglimin: A potential new mutli-target drug for type 2 diabetes," Drugs in Rand D vol. 15, Issue 3, pp. 227-232, 2015.

Vuylsteke, V., et al., "Imeglimin: A potential new mutli-target drug for type 2 diabetes," *Drugs in Rand D* 15(3): 227-32, Adis International Ltd., United Kingdom (2015).

World Health Organization, "International Nonproprietary Names for Pharmaceutical Substances (INN)," WHO Drug Information, pp. 1-56, 2007.

Yancy, C.W., et al., "Clinical presentation, management, and in-hospital outcomes of patients NPL39 admitted with acute decompensated heart failure with preserved systolic function: a report from the Acute Decompensated Heart Failure National Registry (ADHERE) Database," *J Am College Cardiol* 47(1):76-84, Elsevier, Netherlands (2006).

Ziegler, A., et al., "Seroconversion to Multiple Islet Autoantibodies and Risk of Progression to Diabetes in Children," Journal of the American Medical Association, vol. 309, Issue 23, pp. 2473-2479, 2013.

(56) References Cited

OTHER PUBLICATIONS

U.S. Appl. No. 16/813,436, filed Mar. 9, 2020, Bill Symonds et al.
U.S. Appl. No. 16/652,911, filed Apr. 1, 2020, Sophie Hallakou-Bozec.
U.S. Appl. No. 17/584,601, filed Jan. 26, 2022, Bill Symonds et al.
G. Vial, et al., Imeglimin Normalizes Glucose Tolerance and Insulin Sensitivity and Improves Mitochondrial Function in Liver of a High-Fat, High-Sucrose Diet Mice Model, Diabetes, Jun. 2015, 64(6), 2254-64.
C. Rhodes, "Type 2 Diabetes—A Matter of B-Cell Life and Death?" Jan. 2005, vol. 307, Science, p. 380-4.
PCT/EP2019/065158 International Search Report dated Dec. 8, 2019.

\* cited by examiner

FILM-COATED TABLET COMPRISING A TRIAZINE DERIVATIVE FOR USE IN THE TREATMENT OF DIABETES

FIELD OF THE INVENTION

This invention pertains to a film-coated tablet comprising an inner core and an external coating, wherein the inner core comprises a high proportion of a specific triazine derivative and a specific binder. It is also directed to the use of these tablets in the treatment of diabetes and/or complications thereof. This invention is further directed to a specific process for the manufacture of these film-coated tablets, which involves a granulation step in a high-shear mixer.

BACKGROUND OF THE INVENTION

Diabetes mellitus is a chronic metabolic disorder of multiple aetiology, characterized by chronic hyperglycaemia with disturbance of carbohydrate, fat and protein metabolism resulting from defects in insulin secretion, insulin action, or both. The effect of diabetes mellitus includes long-term damage, dysfunction and failure of various organs. Diabetes mellitus is usually divided into two major categories:
  Type 1 diabetes (formerly insulin-dependent diabetes mellitus) usually develop in childhood or adolescence and are prone to ketosis and acidosis. Type 1 diabetes accounts for around 10% of all diabetes.
  Type 2 diabetes (formerly non-insulin-dependent diabetes mellitus) includes the common major form of diabetes which results from defect(s) in insulin secretion, almost always with a major contribution from insulin resistance. Type 2 diabetes accounts for around 90% of all diabetes.

One of the primary progenitors of type 2 diabetes is presumed to be progressive beta cell dysfunction, which appears early in the clinical course (perhaps antedating and even contributing to the development of insulin resistance) and progressively worsens even under treatment. In type 2 diabetes, the beta cells of the pancreas fail to produce enough insulin to meet the body's demand, in part because of an acquired decrease in beta cell mass. It appears that increased beta cell apoptosis is an important factor contributing to beta cell loss and the onset of type 2 diabetes (Rhodes CJ., Science, 2005, Jan. 21; 307(5708):380-4). This happens by numerous mechanisms, including the generation of reactive oxygen species, alterations in metabolic pathways, increases in intracellular calcium and the activation of endoplasmic reticulum stress. These processes adversely affect beta cells by impairing insulin secretion, decreasing insulin gene expression and ultimately causing apoptosis.

Mitochondria also play an essential role in the pathophysiology of diabetes. They are the power stations of the body's cells, contributing to the regulation of energy balance and metabolism. The principal role of mitochondria is to produce energy in the form of an adenosine tri-phosphate (ATP) molecule by oxidizing nutrients such as glucose and fatty acids from food. In diabetes pathophysiology, metabolic misbalance creates a pressure onto the mitochondria, which leads to their dysfunction, reduction of oxidative capacity, and subsequently to the accumulation of lipids in insulin-sensitive tissues and, lastly, to insulin resistance and diabetes.

Type 2 diabetes can affect many major organs, including heart, blood vessels, nerves, eyes and kidneys leading to various diseases, including cardiovascular diseases, neuropathy, ulcers, retinopathy and nephropathy. Treatments that offer durable glycemic control could thus reduce complications associated with type 2 diabetes.

International patent application WO2001/055122 describes triazine derivatives and their hypoglycaemic properties. Among these triazine derivatives, the Applicant has shown that 2-amino-3,6-dihydro-4-dimethylamino-6-methyl-1,3,5-triazine hydrochloride (also known as "imeglimin") was efficient at protecting beta cells from cellular death, and could consequently be useful in the treatment of type 2 diabetes or for preventing or delaying beta cell dysfunction in at risk population before the onset of type 2 diabetes, in particular for subjects having pre-diabetes (WO 2011/154497). In addition, it was demonstrated that Imeglimin stimulates muscle glucose uptake and normalizes glucose tolerance and insulin sensitivity by protecting mitochondrial function from oxidative stress and favoring lipid oxidation in the liver (G. Vial et al., *Diabetes*, 2015, 64(6), 2254-64). Due to its mitochondrial effects, Imeglimin may in particular help prevent micro- and macrovascular complications in type 2 diabetes.

By acting on both insulin resistant organs (liver and muscle) and insulin secretion (via pancreatic β-cells) imeglimin thus targets the key defects of type 2 diabetes.

Various formulations and manufacturing processes have been proposed for the manufacture of imeglimin tablets. For instance, it has been suggested in (WO 2010/066326) to form a mixture of the triazine derivative with various excipients, then wet granulating this mixture by wetting it with a binder, then lubricating the resulting granules before pressing the lubricated mixture to give tablets.

It was determined during clinical studies that the optimal daily dose of imeglimin to be administered orally would exceed 1000 mg, which could correspond to the daily intake of several tablets with 500 mg or 750 mg dosage strength per unit, respectively. However, 750 mg tablets prepared as suggested above with conventional excipients generally weigh about 1000 mg per tablet (see for instance the examples provided in WO 2011/154497) and are accordingly too large for patients having difficulties in swallowing including, but not limited to, elderly people. Since this large size may negatively affect treatment compliance, improvements in the administrability of imeglimin tablets has thus been required without detrimentally affecting its chemical stability and its dissolution rate.

SUMMARY

A first object of this invention is to provide a tablet formulation allowing to include at least 500 mg of a triazine derivative such as imeglimin in a tablet, wherein the triazine derivative represents at least 80 wt. % of the tablet and is chemically stable.

A second object of this invention is to provide a tablet containing a triazine derivative such as imeglimin, which is physically stable, as reflected by its resistance to crushing or hardness, while allowing immediate release of imeglimin in stomach, as reflected by its dissolution rate.

A third object of this invention is to provide a manufacturing process of this tablet, which can be easily and reproducibly performed on an industrial scale.

In an attempt to reduce the size of imeglimin tablets, the present inventors conducted extensive research regarding the nature and level of excipients and the method of incorporating the same. As a result, they found an optimal combination of ingredients that may be mixed with imeglimin to form tablets and a specific process for preparing these tablets in which conventional wet granulation methods in fluidized bed are substituted with wet granulation in a high-shear mixer.

This invention is thus directed to a film-coated tablet comprising:
(a) an inner core comprising:
a triazine derivative selected from the group consisting of 2-amino-3,6-dihydro-4-dimethylamino-6-methyl-1,3,5-triazine and pharmaceutically acceptable salts thereof, in an amount of at least 80 wt. %, relative to the total weight of the tablet,
at least one binder comprising hydroxypropylcellulose,
at least one glidant,
at least one disintegrant, and
at least one lubricant; and
(b) an external coating comprising at least one water-soluble film-forming agent.

It also pertains to a process for the manufacture of this film-coated tablet, comprising the following successive steps:
1) wet granulating the triazine derivative with hydroxypropylcellulose and optionally part of the glidant, in a high-shear mixer, using water as a granulation aid,
2) drying the granules,
3) mixing the granules with the remaining excipients,
4) compressing the resulting mixture on a tableting machine, and
5) coating the tablets thus obtained.

This invention further pertains to the film-coated tablet as described above for use in the treatment of diabetes and/or complications thereof.

DETAILED DESCRIPTION

Tablet Composition

By "tablet", it is meant any shaped and compressed solid dosage form, including caplets.

The tablet of this invention comprises, as an active pharmaceutical ingredient, a triazine derivative (a tetrahydrotriazine) belonging to the chemical class of the glimins and corresponding to 2-amino-3,6-dihydro-4-dimethylamino-6-methyl-1,3,5-triazine and its salts. This compound may for instance be synthetized as described in WO 2009/095159, WO 2012/072663, WO 2010/012746, WO 2009/141040, or a combination thereof.

The compounds of the present invention contain an asymmetric centre. This asymmetric centre may be in R or S configuration. In addition, these compounds also exhibit tautomerism, as can be shown below:

It should be understood that the present invention includes individual tautomers, geometrical isomers, optical isomers and mixtures thereof, including racemic mixtures, of these triazine derivatives. Optical isomers can be separated from mixtures thereof by application or adaptation of known processes, for example chromatography or recrystallisation techniques, or they can be prepared separately from suitable isomers of their intermediates, as described in the above patent applications.

The triazine derivative of this invention is thus selected from the group consisting of (+)-2-amino-3,6-dihydro-4-dimethylamino-6-methyl-1,3,5-triazine and pharmaceutically acceptable salts thereof; (−)-2-amino-3,6-dihydro-4-dimethylamino-6-methyl-1,3,5-triazine and pharmaceutically acceptable salts thereof; and their mixtures.

More specifically, the triazine derivative is selected from the group consisting of (+)-2-amino-3,6-dihydro-4-dimethylamino-6-methyl-1,3,5-triazine and pharmaceutically acceptable salts, optionally mixed with (−)-2-amino-3,6-dihydro-4-dimethylamino-6-methyl-1,3,5-triazine and pharmaceutically acceptable salts thereof in a (+):(−) weight ratio of at least 95:5.

When the triazine derivative is in a form of a pharmaceutically acceptable salt, the salt can include salts with any inorganic acid, salts with any organic acid, and salts with any acidic amino acid. Useful examples of the salt with inorganic acid include salts with hydrochloric acid, hydrobromic acid, nitric acid, sulfuric acid, and phosphoric acid. Useful examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, and p-toluenesulfonic acid. Preferably, the triazine derivative is administered in the form of a hydrochloride salt.

(+)-2-amino-3,6-dihydro-4-dimethylamino-6-methyl-1,3,5-triazine hydrochloride is also called imeglimin. It is usually prepared in the form of the following stable tautomer:

also referred to as 5,6-dihydro-4-dimethylamino-2-imino-6-methyl-1,2,3-triazine.

The present patent application also pertains to the polymorphic forms of the compounds, for instance the A1 or H1 polymorphic forms of the (+)-2-amino-3,6-dihydro-4-dimethylamino-6-methyl-1,3,5-triazine hydrochloride salt, preferably the A1 form thereof.

The triazine derivative may represent at least 80 wt. %, preferably at least 85 wt. % or even at least 90 wt. %, relative to the total weight of the tablet.

In the tablet of this invention, the triazine derivative is mixed with at least one binder comprising hydroxypropylcellulose, The viscosity of HPC is typically between 300.0 and 600.0 mPa·s when measured at 20° C. as a 10 wt. % solution in water.

In a preferred embodiment, the binder consists of hydroxypropylcellulose. In other embodiments, it may comprise at least one other binder in addition to hydroxypropylcellulose, which may be selected from: microcrystalline cellulose, methylcellulose, ethylcellullose, hydroxyethylcellulose, hydroxypropylmethylcellulose (hypromellose), sodium carboxymethylcellulose (carmellose), gelatin, gum arabic, dextrin, maltodextrin, pregelatinized starch, gelatin, acacia gum, guar gum, sodium alginate, alginic acid, carbomer, polyvinyl alcohol and mixtures thereof. Preferably, the binder does not comprise polyvinylpyrrolidone (povidone). Compatibility tests have indeed shown that degradation products are formed when imeglimin is mixed with this excipient as a 50:50 (w/w) binary mixture. The binder(s) may represent from 1.5 to 4.5 wt. %, preferably from 3.5 to 4.5 wt. %, relative to the total weight of the tablet.

In addition to the binder(s), the tablet of this invention comprises at least one disintegrant. Preferably, the disintegrant does not comprise crospovidone. Compatibility tests have indeed shown that degradation products are formed when imeglimin is mixed with this excipient as a 50:50 (w/w) binary mixture. The disintegrant may thus be selected from the group consisting of: sodium croscarmellose, sodium carboxymethyl starch, hydroxypropylcellulose, calcium carboxymethylcellulose, microcrystalline cellulose, calcium carbonate, magnesium aluminum silicate, sodium starch glycolate, pregelatinized starch, sodium alginate, alginic acid, guar gum and their mixtures, for instance. Preferably, the disintegrant comprises, or preferably is, sodium croscarmellose. The disintegrant(s) may represent from 1.5 to 3 wt. %, preferably from 1.8 to 2.2 wt. %, relative to the total weight of the tablet.

The tablet of this invention further comprises at least one glidant, which may be selected from the group consisting of: anhydrous colloidal silica (also called fumed silica), magnesium stearate, starch, talc and mixtures thereof. Preferably, the glidant comprises, or preferably is, anhydrous colloidal silica. The glidant(s) may represent from 0.8 to 2.5 wt. %, preferably from 1.8 to 2.2 wt. %, relative to the total weight of the tablet.

At least one lubricant is also comprised within the tablet of this invention, which may for instance be selected from the group consisting of: magnesium stearate, calcium stearate, stearic acid, sodium stearyl fumarate, sucrose fatty acid ester, talc, and mixtures thereof. Preferably, the lubricant is magnesium stearate. The lubricant(s) may represent from 0.5 to 1.5 wt. %, preferably from 0.8 to 1.2 wt. %, relative to the total weight of the tablet.

In order to make the ingestion of the tablet easier and to mask the bitterness of the triazine derivative, the tablet is coated with an external coating comprising at least one water-soluble film-forming agent. The water-soluble film-forming agent may be an acrylic polymer or a cellulosic polymer, preferably hydroxypropylmethylcellulose, and the coating optionally further includes at least one compound selected from opacifying and/or coloring agent, such as titanium dioxide and iron oxides, plasticizing agents, such as polyethylene glycols, fillers, such as lactose and microcrystalline cellulose, sweeteners, such as saccharin sodium, lubricants, such as talc, surfactants, and mixtures thereof.

Commercial products corresponding to such mixtures are available including the products marketed under the trade name Opadry® and Opadry® II. Nonlimiting examples include Opadry® YS-1-7706-G white, Opadry® Yellow 03692357 and Opadry® Blue 03690842). These compositions are available as dry film coating compositions that can be diluted in water shortly before use. Opadry® and Opadry® II formulations comprise a cellulosic film forming polymer (e.g., HPMC and/or HPC), and may contain polydextrose, maltodextrin, a plasticizer (e.g., triacetin, polyethylene glycol), polysorbate 80, a colorant (e.g., titanium dioxide, one or more dyes or lakes), and/or other suitable film-forming polymers (e.g., acrylate-methacrylate copolymers). Particularly preferred commercial products are Opadry® White (HPMC/HPC-based) and Opadry® II White (PVA/PEG-based). Alternative products for initial protective coats include polyvinyl alcohol-polyethylene glycol graft copolymers such as the product available commercially under the name Kollicoat® IR and methyl methacrylate ammonium-based copolymers such as the products available commercially under the name Eudragit® E. Another preferred example is low molecular weight HPMC.

The coating may represent from 2 to 3 wt. %, preferably from 2.2 to 2.8 wt. %, relative to the total weight of the tablet.

Additional excipients may be included within the tablet, such as sweeteners, flavoring agents, coloring agents, plasticizers, diluents and the like. However, according to a preferred embodiment, the tablet of this invention does not comprise any other excipient than those listed above.

In a particularly preferred embodiment, the tablet of this invention consists of:
triazine derivative: 85-95 wt. %
binder(s): 1.5-4.5 wt. %
disintegrant(s): 1.5-3 wt. %
glidant(s): 0.8-2.5 wt. %
lubricant(s): 0.5-1.5 wt. %
coating: 2-3 wt. %
provided that the total content of the above ingredients amounts to 100 wt. %.

The tablet of this invention may have any shape such as an ellipsoidal, round, square or diamond shape. An ellipsoidal biconvex shape is preferred. Each tablet usually contains from 250 to 1000 mg of triazine derivative, preferably 500 or 750 mg.

The triazine derivative contained in this tablet is chemically stable, i.e.:
it generates less than 2.0 wt. %, preferably less than 1 wt. %, still preferably less than 0.5 wt. %, for instance less than 0.1 wt. % or even less than 0.05 wt. % of total degradation products, as measured by HPLC, after six months storage at 40° C./75% HR in a blister, and
the amount of triazine derivative remains between 90 and 105% of its theoretical value, under the same conditions, as also measured by HPLC.

In addition, the dissolution rate of the triazine derivative, as measured according to the method provided in the following Examples, is between 80 and 100%, preferably between 90 and 100, more preferably from 95 to 100%, within 30 minutes in an aqueous buffered medium.

Manufacturing Process

The process for the manufacture of the film-coated tablets described above will now be described.

In the first step of this process, the triazine derivative is wet granulated with hydroxypropylcellulose in a high-shear mixer, using water as a granulation aid. Part of the glidant may be added at this stage, in order to lower the risk for the triazine derivative to agglomerate during the manufacturing process, although this is not compulsory. The whole amount of glidant may alternatively be provided at a later stage in the process.

Granules are thus obtained, which are dried by any suitable means, for example in a fluid-bed dryer, in the second step of this process. Since water improves the cohesion of the granules but at the same time enhances the stickiness of the triazine derivative, it is desirable to adjust the drying step so as to reach less than 2% residual water in the granules, preferably less than 1.5% and still preferably less than 1%. Their moisture content may be measured by the Karl-Fischer Method, in accordance with Ph. Eur. 2.5.12. The amount of binder will usually be adjusted depending on the intended water content of the dried granules. The lower the amount of water is, the higher the content of binder should be.

The dried granules are then mixed with the remaining excipients, optionally after sieving.

The resulting mixture is compressed on a tableting machine, such as a rotary press so as to obtain tablet cores having for instance a hardness of at least 60 N, for instance ranging from 100 to 200 N, as measured according to Ph. Eur. 2.9.8.

These tablet cores are then coated with the water-soluble film-forming agent. For this purpose, the film forming agent may be used as an aqueous solution.

As evident from the foregoing, water is the only solvent used respectively as a granulation aid in the granulation step and as a dispersing agent in the coating step and it is removed during the process by drying. The process of this invention may thus be conducted using well tolerated excipients in cost-effective conditions.

Pharmaceutical Uses

The film-coated tablet as described above may be used as a medicament, preferably in the treatment of diabetes and/or complications thereof.

Within the context of the invention, the term treatment denotes curative, symptomatic, and/or preventive treatments. In particular, it can refer to reducing the progression of the disease, reducing or suppressing at least one of its symptoms or complications (including cardiovascular diseases, neuropathy, ulcers, retinopathy or nephropathy), or improving in any way the state of health of patients. The triazine derivatives of the invention can be used in humans with existing type 2 diabetes, including at early or late stages of the disease, preferably at early stage of the disease. The derivatives of the invention will not necessarily cure the patient who has the disease but will delay or slow the progression or prevent further progression of the disease, ameliorating thereby the patients' condition. The derivatives of the invention can also be administered to those who do not have all symptoms of type 2 diabetes but who would normally develop the type 2 diabetes or be at increased risk for type 2 diabetes. Treatment also includes delaying the development of the disease in an individual who will ultimately develop all symptoms of type 2 diabetes or would be at risk for the disease due to age, familial history, genetic or chromosomal abnormalities, and/or due to the presence of one or more biological markers for the disease.

In treating type 2 diabetes, the derivatives of the invention are administered in a therapeutically effective amount, i.e. in a daily dose ranging from 500 to 3000 mg, for instance. In the present invention, an "effective amount" is an amount sufficient to improve in any way the state of health of the patient. The triazine derivative may be administered once a day, twice a day or three times a day, preferably twice a day. Still preferably, 500 mg or 750 mg of the triazine derivative is administered twice a day.

As mentioned before, type 2 diabetes can affect many major organs, including heart, blood vessels, nerves, eyes and kidneys. Complications associated with type 2 diabetes can correspond to various diseases, such as for instance cardiovascular diseases, neuropathy, ulcers (i.e., foot ulcers), retinopathy or nephropathy. Cardiovascular diseases include more particularly high blood pressure, coronary artery disease, heart disease and/or stroke.

The medicament for treating type 2 diabetes comprising a triazine derivative according to the invention is administrated to a subject in need thereof.

Subjects in need of such treatment may be diagnosed by implementing the following tests:

A fasting plasma glucose (FPG) test measures blood glucose in a person who has not eaten anything for several hours, such as for at least 8 hours. This test is used to detect diabetes and pre-diabetes.

An oral glucose tolerance test (OGTT) measures blood glucose after a person fasts at least 8 hours and 2 hours after the person drinks a glucose-containing beverage. This test can be used to diagnose diabetes and pre-diabetes.

A random plasma glucose test, also called a casual plasma glucose test, measures blood glucose without regard to when the person being tested last ate. This test, along with an assessment of symptoms, is used to diagnose diabetes but not pre-diabetes.

Test results indicating that a subject has diabetes could be confirmed with a second test on a different day.

Depending on the obtained test results, subjects can be diagnosed as being normal, pre-diabetes or diabetes subjects. Pre-diabetes precedes the onset of type 2 diabetes. Generally, subjects who have pre-diabetes have fasting blood glucose levels that are higher than normal, but not yet high enough to be classified as diabetes. Pre-diabetes greatly increases the risk for diabetes.

In a specific embodiment, subjects in need of the treatment of the invention are subjects having pre-diabetes or type 2 diabetes.

In another specific embodiment, subjects in need of the treatment of the invention have gestational diabetes.

The triazine derivative according to an embodiment of the invention may be co-administered with at least one other active compound. Preferably, the at least one other active compound is chosen among treatments currently used to treat pre-diabetes or type 2 diabetes. The term "co-administration" (or "co-administrered") means the simultaneous, separate or sequential administration of one or more compounds to the same patient, over a period that may be up to 2 hours or even up to 12 hours. For example, the term co-administration includes (1) a simultaneous administration of both compounds, (2) an administration of the first, followed 2 hours later by the administration of the second compound, (3) an administration of the first, followed 12 hours later by the administration of the second compound.

Examples of active compounds that may be co-administered with the triazine derivative of this invention include alpha-glucosidase inhibitors, e.g., acarbose and miglitol; insulin sensitisers, e.g., thiazolidinediones (TZD), such as pioglitazone and rosiglitazone; agents that reduce glucogenesis, e.g., biguanides, such as metformin; sulfonylureas (SU) such as carbutamide, glibenclamide/glyburide, glibomuride, gliclazide, glimepiride, glipizide, chlorpropamide, and tolazamide; glinides such as repaglinide; dopamine agonists, such as bromocriptine; DPP-4 inhibitors such as alogliptin, linagliptin, saxagliptin, sitagliptin, or vildagliptin; sodium glucose transporter (SGLT2 or SGLT 1/2) inhibitors such as dapagliflozin, canagliflozin, empagliflozin, or sotagliflozin.

In any case, the tablets according to this invention may be packaged in blisters, such as PCTFE, PVC, PVDC, PVC/PE/PVDC or aluminium blisters; or in plastic bottles such as PE or PP bottles.

EXAMPLES

This invention will be better understood in light of the following examples which are given for illustrative purposes only and do not intend to limit the scope of the invention, which is defined by the attached claims.

Example 1: Manufacture of Tablets According to this Invention

Four tablets having the following compositions were prepared.

| Constituent | Tablets 1 | | Tablets 2 | |
|---|---|---|---|---|
| Imeglimin | 500 mg | 750 mg | 500 mg | 750 mg |
| Hydroxypropylcellulose | 10.87 mg | 16.30 mg | 21.9 mg | 33.0 mg |
| Sodium croscarmellose | 11.18 mg | 16.77 mg | 10.4 mg | 16.0 mg |
| Anhydrous colloidal silica (Aerosil ® 200) | 5.05 mg | 7.58 mg | 10.6 mg | 15.8 mg |
| Magnesium stearate | 5.33 mg | 8.00 mg | 5.5 mg | 8.2 mg |
| Opadry ® [1] | 13.53 mg | 20.30 mg | 14.0 mg | 21.0 mg |
| Total | 546.0 mg | 819.00 mg | 562.4 mg | 844.0 mg |

[1] Hypromellose, polyethylene glycol, saccharin sodium, talc and titanium dioxide.

Tablets 1 were manufactured according to a process comprising a first step of preparing a premix of imeglimin with anhydrous colloidal silica, then mixing this premix with hydroxypropylcellulose in a high-shear mixer. The granules thus obtained were dried with a fluid-bed dryer. The dried granules had a moisture content of about 0.8-1.0%, as measured by the Karl-Fischer Method, in accordance with Ph. EUR 2.5.12. They were then sieved and mixed with sodium croscarmellose and magnesium stearate within a container blender to obtain the final blend. This blend was compressed on a standard rotary press. The tablets cores thus obtained were then film-coated with an aqueous suspension of Opadry® in a standard coater. Tablets 2 were prepared similarly, except that anhydrous colloidal silica was added to the extragranular materials instead of being premixed with imeglimin.

Example 2: Comparative Tablets

Tablets of two different strengths having the following compositions were prepared.

| Constituent | Amount | Amount |
|---|---|---|
| Imeglimin | 500 mg | 750 mg |
| Gelatin | 27.8 mg | 41.7 mg |
| Microcrystalline cellulose | 134.1 mg | 201.2 mg |
| Anhydrous colloidal silica (Aerosil ® 200) | 10.2 mg | 15.4 mg |
| Sodium croscarmellose | 21.0 mg | 31.5 mg |
| Magnesium stearate | 7.0 mg | 10.5 mg |
| Opadry ® [1] | 17.5 mg | 24.7 mg |
| Total | 717.6 mg | 1075.0 mg |

[1] Hypromellose, polyethylene glycol, saccharin sodium, talc and titanium dioxide These tablets were prepared as follows.

Granules of imeglimin were prepared by using a premix of imeglimin with 50 wt. % of the silica, which was wet granulated using a standard process comprising fluid-bed granulation. Gelatin suspended in water was used as a granulation aid. The granules were dried within the fluid-bed granulator and then sieved and mixed with the remaining components within a contained blender to get the final blend. The ready-to-press mixture was compressed on a standard rotary press. The tablet cores thus obtained were then film-coated with an aqueous suspension of Opadry® in a standard coater.

As can be seen from the above table, these conventional tablets are much heavier and thus larger than the tablets according to this invention, which makes them difficult to swallow.

Example 3: Dissolution Tests

Dissolution rates indicative of bioavailability were performed according to US Pharmacopoeia <711> and European Pharmacopoeia 2.9.3 version using a paddle apparatus with a stirring speed of 75 rpm, a 900 mL sample and a buffer adjusted to pH 6.8. The dissolved concentration of imeglimin is determined minimal at a specified time point from each vessel by UV detection at 240 nm. The results of this experiment are provided in the following table for Tablets 1 and 2 of Example 1 when stored in PVC/PE/PVDC blisters under different conditions.

| | Dissolution (%) within 30 min | | | |
|---|---|---|---|---|
| | Tablets 1 (500 mg) | | Tablets 2 (500 mg) | |
| Time | 40° C./75% HR | 30° C./65% HR | 40° C./75% HR | 30° C./65% HR |
| 0 month | 101 | 101 | 99 | 99 |
| 3 months | 98 | — | 101 | 99 |
| 6 months | 99 | 100 | 100 | 99 |

From this table it appears that imeglimin fully dissolves within 30 min and that this dissolution rate is stable with time. The tablets of this invention may thus allow immediate release of imeglimin within the stomach.

Figure 1:
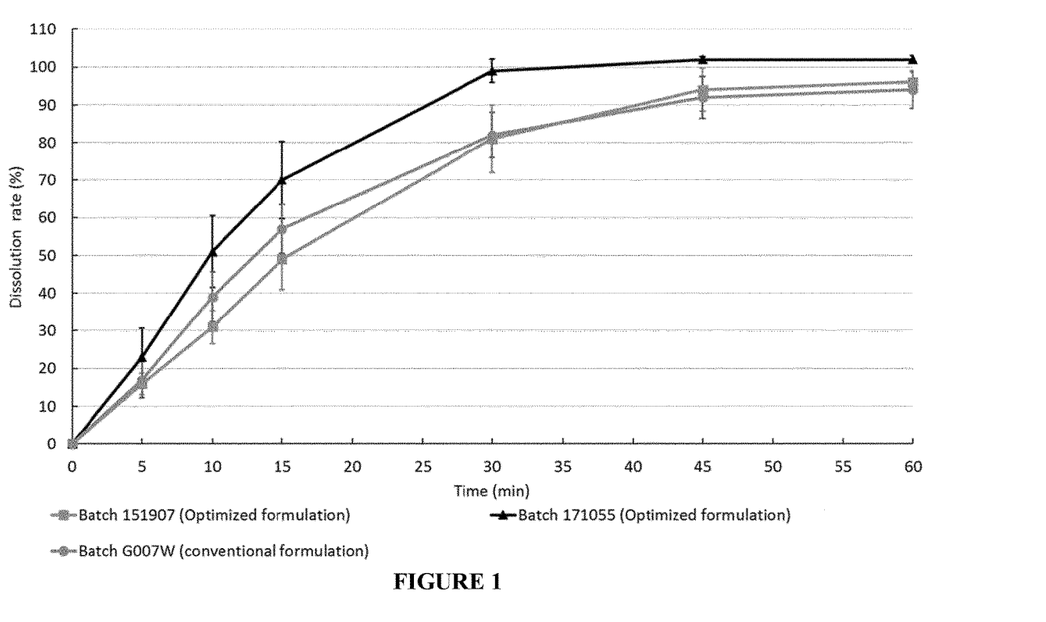
FIG. 1 shows the dissolution rates of two tablets of this invention (optimized tablets) compared with that of conventional tablets, at pH 1.2.
Figure 2:
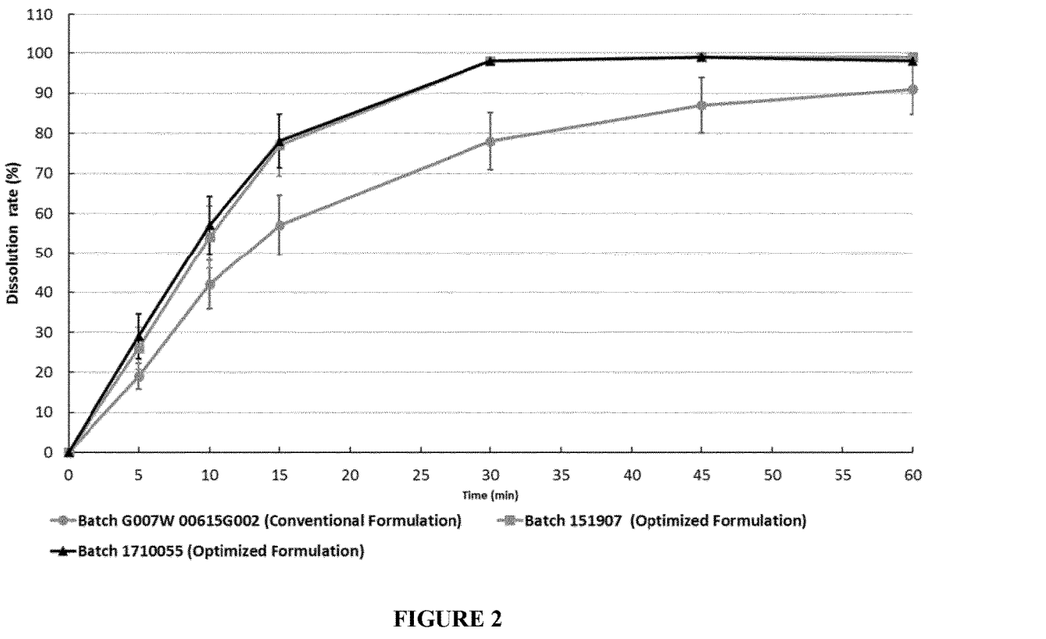
FIG. 2 shows the dissolution rates of two tablets of this invention (optimized tablets) compared with that of conventional tablets, at pH 6.8.

Additional dissolution experiments were performed to compare the dissolution rates of the tablets according to this invention, as described in Example 1, with that of the conventional 500 mg tablets as described in Example 2. These experiments were conducted according to US Pharmacopoeia <711> and European Pharmacopoeia 2.9.3 version using a paddle apparatus with a stirring speed of 50 rpm, a 900 mL sample and a buffer adjusted either to pH 1.2 or to pH 6.8. The dissolved concentration of imeglimin is determined minimal at a specified time point from each vessel by UV detection at 240 nm. The results of these experiments are illustrated on FIGS. 1 and 2, wherein Batch 151907 refers to Tablet 1 and Batch 171055 refers to Tablet 2. As shown on these Figures, the dissolution rates of Tablets 1 and 2 is similar to, or even greater than, that of the conventional tablets, both at pH 1.2 and at pH 6.8.

Example 4: Stability Tests

The variation in imeglimin content and total degradation products over time for Tablets 1 and 2 of Example 1 were assessed by HPLC suitable for gradient elution and UV detection at 215 nm. The calculation was done against an external standard. The results of these experiments are reported in the following table.

|  | Assay of imeglimin (%) | | | | Total degradation products (%) | | | |
| --- | --- | --- | --- | --- | --- | --- | --- | --- |
|  | Tablets 1 (500 mg) | | Tablets 2 (500 mg) | | Tablets 1 (500 mg) | | Tablets 2 (500 mg) | |
| Time | 40° C./ 75% HR | 30° C./ 65% HR | 40° C./ 75% HR | 30° C./ 65% HR | 40° C./ 75% HR | 30° C./ 65% HR | 40° C./ 75% HR | 30° C./ 65% HR |
| 0 month | 97 | 97 | 97 | 97 | 0.08 | 0.08 | <0.05 | <0.05 |
| 3 months | 100 | — | 98 | 97 | <0.05 | — | <0.05 | <0.05 |
| 6 months | 99 | 98 | 98 | 98 | 0.06 | 0.15 | <0.05 | 0.06 |

These results demonstrate that imeglimin is chemically stable over time, with a content of active compound which remains within the 90-105% range and a content of total degradation products which remains well below 2.0%.

The invention claimed is:
1. A film-coated tablet comprising:
  (a) an inner core comprising:
    at least 85 wt. % of a triazine derivative 2-amino-3,6-dihydro-4-dimethylamino-6-methyl-1,3,5-triazine or pharmaceutically acceptable salts thereof, relative to the total weight of the tablet,
    hydroxypropylcellulose as a binder,
    at least one glidant,
    at least one disintegrant, and
    at least one lubricant;
    wherein the inner core is substantially free of povidone and crospovidone; and
  (b) an external coating comprising at least one water-soluble film-forming agent.
2. The film-coated tablet according to claim 1, characterized in that the triazine derivative is selected from the group consisting of (+)-2-amino-3,6-dihydro-4-dimethylamino-6-methyl-1,3,5-triazine and pharmaceutically acceptable salts thereof; (−)-2-amino-3,6-dihydro-4-dimethylamino-6-methyl-1,3,5-triazine and pharmaceutically acceptable salts thereof; and their mixtures.
3. The film-coated tablet according to claim 2, characterized in that the triazine derivative is selected from the group consisting of (+)-2-amino-3,6-dihydro-4-dimethylamino-6-methyl-1,3,5-triazine and pharmaceutically acceptable salts, optionally mixed with (−)-2-amino-3,6-dihydro-4-dimethylamino-6-methyl-1,3,5-triazine and pharmaceutically acceptable salts thereof in a (+):(−) weight ratio of at least 95:5.
4. The film-coated tablet according to claim 1, characterized in that the pharmaceutically acceptable salt is a hydrochloride salt.
5. The film-coated tablet according to claim 1, characterized in that the water-soluble film-forming agent is an acrylic polymer or a cellulosic polymer, and the coating optionally further includes at least one compound selected from an opacifying and/or coloring agent, plasticizing agents, fillers, sweeteners, lubricants, surfactants, and mixtures thereof.
6. The film-coated tablet according to claim 1, characterized in that the tablet comprises from 250 to 1000 mg of the triazine derivative.
7. The film-coated tablet according to claim 1, characterized in that the glidant is selected from the group consisting of: anhydrous colloidal silica, magnesium stearate, starch, talc, and mixtures thereof.
8. The film-coated tablet according to claim 1, characterized in that the disintegrant is selected from the group consisting of: sodium croscarmellose, sodium carboxymethyl starch, hydroxypropylcellulose, calcium carboxymethylcellulose, microcrystalline cellulose, calcium carbonate, magnesium aluminum silicate, sodium starch glycolate, pregelatinized starch, sodium alginate, alginic acid, guar gum, and their mixtures.
9. The film-coated tablet according to claim 1, characterized in that the lubricant is selected from the group consisting of: magnesium stearate, calcium stearate, stearic acid, sodium stearyl fumarate, sucrose fatty acid ester, talc, and mixtures thereof.
10. The film-coated tablet according to claim 1, characterized in that the binder consists of hydroxypropylcellulose.
11. The film-coated tablet according to claim 1, characterized in that it comprises:
  triazine derivative: at least 85 wt. %;
  hydroxypropylcellulose: 1.5-4.5 wt. %;
  disintegrant(s): 1.5-3 wt. %;
  glidant(s): 0.8-2.5 wt. %;
  lubricant(s): 0.5-1.5 wt. %; and
  coating: 2-3 wt. %,
provided that the total content of the above ingredients amounts to 100 wt. %.
12. A process for the manufacture of the film-coated tablet according to claim 1, comprising the following successive steps:
  1) Wet granulating the triazine derivative with hydroxypropylcellulose and optionally part of the glidant, in a high-shear mixer, using water as a granulation aid,
  2) drying the granules,
  3) mixing the granules with the remaining excipients,
  4) compressing the resulting mixture on a tableting machine, and
  5) coating the tablets thus obtained.
13. A method of treating diabetes or complications thereof in a subject, the method comprising administering to the subject the film coated tablet according to claim 1.
14. The film-coated tablet according to claim 5, wherein the water-soluble film-forming agent is hydroxypropylmethylcellulose.
15. The film-coated tablet according to claim 6, wherein the tablet comprises about 500 mg or about 750 mg of the triazine derivative.

16. The film-coated tablet according to claim 7, wherein the glidant is anhydrous colloidal silica.

17. The film-coated tablet according to claim 8, wherein the disintegrant is sodium croscarmellose.

18. The film-coated tablet according to claim 9, wherein the lubricant is magnesium stearate.

19. The film-coated tablet according to claim 1, wherein the triazine derivative is 2-amino-3,6-dihydro-4-dimethyl-amino-6-methyl-1,3,5-triazine or hydrochloride salt thereof, the binder is hydroxypropyl cellulose, the disintegrant is sodium croscarmellose, the lubricant is magnesium stearate and the glidant is anhydrous colloidal silica.

20. The film-coated tablet of claim 1, which generates less than 2.0 wt. % of total degradation products, as measured by HPLC, after six-month storage at 40° C./75% HR in a packaging blister.

21. An oral film-coated tablet comprising
an inner core which is substantially free of crospovidone and povidone and which comprises:
at least 85 wt. % of 2-amino-3,6-dihydro-4-dimethyl-amino-6-methyl-1,3,5-triazine or hydrochloride salt thereof,
at least 1.5 wt. % of hydroxypropylcellulose,
from 1.5 to 3 wt. % of sodium croscarmellose,
from 0.8 to 2.5 wt. % of anhydrous colloidal silica, and
from 0.5 to 1.5 wt. % of magnesium stearate,
the percentage being relative to the total weight of the tablet; and
an external coating accounting for 2 to 3 wt. % of the total weight of the tablet and comprising at least one water-soluble film-forming agent.

22. The film-coated tablet of claim 21, which generates less than 2.0 wt. % of total degradation products, as measured by HPLC, after six-month storage at 40° C./75% HR in a packaging blister.

23. The film-coated tablet of claim 1, wherein hydroxypropylcellulose accounts for at least 1.5% by weight relative to the total weight of the tablet.

\* \* \* \* \*